(12) United States Patent
Huang et al.

(10) Patent No.: US 11,986,243 B2
(45) Date of Patent: May 21, 2024

(54) FUNDUS CAMERA (71) Applicant: SHENZHEN THONDAR TECHNOLOGY CO., LTD, Guangdong (CN)

(72) Inventors: Yequan Huang, Guangdong (CN); Jianwei Ren, Guangdong (CN); Zhenhua Chen, Guangdong (CN); Xuechuan Dong, Guangdong (CN); Feiyan Ma, Guangdong (CN); Jinsong Zhang, Guangdong (CN); Sha Lai, Guangdong (CN); Kexing Liu, Guangdong (CN); Zeljko Ribaric, Guangdong (CN)

(73) Assignee: SHENZHEN THONDAR TECHNOLOGY CO., LTD, Shenzhen (CN)

( * ) Notice: Subject to any disclaimer, the term of this patent is extended or adjusted under 35 U.S.C. 154(b) by 974 days.

(21) Appl. No.: 16/962,511

(22) PCT Filed: Jan. 22, 2019

(86) PCT No.: PCT/CN2019/072629
§ 371 (c)(1),
(2) Date: Jul. 16, 2020

(87) PCT Pub. No.: WO2019/141283
PCT Pub. Date: Jul. 25, 2019

(65) Prior Publication Data
US 2020/0345229 A1 Nov. 5, 2020

(30) Foreign Application Priority Data
Jan. 22, 2018 (CN) .......................... 201810062785.3

(51) Int. Cl.
*A61B 3/14* (2006.01)
*A61B 3/00* (2006.01)
*A61B 3/12* (2006.01)

(52) U.S. Cl.
CPC .............. *A61B 3/14* (2013.01); *A61B 3/0008* (2013.01); *A61B 3/12* (2013.01)

(58) Field of Classification Search
CPC ........... A61B 3/14; A61B 3/0008; A61B 3/12; A61B 3/152
See application file for complete search history.

(56) References Cited

U.S. PATENT DOCUMENTS

2007/0252951 A1 11/2007 Hammer et al.
2008/0123052 A1 5/2008 Su et al.
(Continued)

FOREIGN PATENT DOCUMENTS

CN 1951314 A 4/2007
CN 102028449 A 4/2011
(Continued)

OTHER PUBLICATIONS

Search report of counterpart European Patent Application No. 19741686.0 dated Sep. 9, 2021.
(Continued)

*Primary Examiner* — George G. King
*Assistant Examiner* — Anna Smith (57) ABSTRACT

Disclosed is a fundus camera, which relates to the technical field of medical devices and includes: an illumination module, a main optical assembly, a focusing module, and an image sensing acquisition module; the illumination module includes a plurality of light sources configured to emit light of different wavelengths, illumination light emitted by the plurality of light sources is conducted to enter an eye of a patient through the main optical assembly, and light reflected
(Continued)

by a retina of the patient is conducted to pass through the main optical assembly and the focusing module to enter the image sensing acquisition module. The fundus camera provided by the present application improves the technical problem that the fundus camera in the prior art cannot image different layers of the retina, thereby providing valuable medical and diagnostic data.

19 Claims, 2 Drawing Sheets

(56) References Cited

U.S. PATENT DOCUMENTS

| | | | |
|---|---|---|---|
| 2011/0299036 A1 | 12/2011 | Goldenholz | |
| 2012/0002167 A1* | 1/2012 | Kondoh | A61B 3/1025 351/211 |
| 2012/0140238 A1 | 6/2012 | Horn et al. | |
| 2015/0002817 A1* | 1/2015 | Alasaarela | A61B 3/14 351/208 |
| 2015/0146168 A1* | 5/2015 | Divo | A61B 3/0091 351/204 |
| 2015/0272432 A1 | 10/2015 | Satake et al. | |
| 2016/0296112 A1 | 10/2016 | Fletcher et al. | |
| 2017/0311796 A1 | 11/2017 | Walsh et al. | |

FOREIGN PATENT DOCUMENTS

| | | | |
|---|---|---|---|
| CN | 104168818 A | 11/2014 | |
| CN | 104412149 A | 3/2015 | |
| CN | 104939802 A | 9/2015 | |
| CN | 205697699 U | 11/2016 | |
| CN | 107126189 A | 9/2017 | |
| CN | 108324240 A | 7/2018 | |
| CN | 208464045 U | 2/2019 | |
| DE | 102012022861 A1 | 5/2014 | |
| DE | 102012022861 A1 * | 5/2014 | ........... A61B 3/0008 |
| EP | 1752084 A2 | 2/2007 | |
| EP | 2374404 A1 | 10/2011 | |
| EP | 2926720 A2 | 10/2015 | |
| WO | 2006016366 A2 | 2/2006 | |
| WO | WO-2006016366 A2 * | 2/2006 | ............... A61B 3/12 |
| WO | 2014149481 A1 | 9/2014 | |
| WO | 2015054672 A1 | 4/2015 | |
| WO | 2016089890 A1 | 6/2016 | |
| WO | WO-2016189890 A1 * | 12/2016 | ............. A61B 3/102 |

OTHER PUBLICATIONS

International Search Report of PCT Patent Application No. PCT/CN2019/072629 dated Apr. 2, 2019.
1st Office Action of counterpart Chinese Patent Application No. 201810062785.3 dated Jul. 27, 2023.

* cited by examiner

FUNDUS CAMERA

CROSS-REFERENCE TO RELATED APPLICATIONS

The present disclosure is the National Stage of International Application with Application No. PCT/CN2019/072629, filed on Jan. 22, 2019, which claims the priority of Chinese Patent Application with No. 201810062785.3, entitled "FUNDUS CAMERA", filed on Jan. 22, 2018, which is hereby incorporated by reference in its entirety.

FIELD

This application relates to the technical field of medical devices, in particular to a fundus camera.

BACKGROUND

The fundus camera is an inspection tool used to observe the fundus of the eyeball, for example, to observe whether the retina, optic disc, and blood vessel distribution are abnormal. Conventional fundus cameras use halogen white light or xenon white light for retinal illumination. The operator uses a light intensity knob to control the retinal illumination. Bright white light flashes through the pupil to the back of the eye. The fundus camera generates color images of the retina through imaging sensing.

SUMMARY

The object of the present application includes providing a fundus camera to improve the technical problem that the fundus camera in the known art cannot image different layers of the retina, thereby providing valuable medical and diagnostic data.

The fundus camera provided in this application includes: an illumination module, a main optical assembly, a focusing module, and an image sensing acquisition module.

The illumination module includes a plurality of light sources configured to emit light of different wavelengths, illumination light emitted by the plurality of light sources is conducted to enter an eye of a patient through the main optical assembly, and light reflected by a retina of the patient is conducted to pass through the main optical assembly and the focusing module to enter the image sensing acquisition module.

Further, the main optical assembly includes a ring reflector and an objective lens, and the ring reflector is arranged obliquely.

The illumination light emitted by the illumination module is reflected to the objective lens by the ring reflector, and then is conducted to enter the eye of the patient. The light reflected by the retina of the patient is conducted to pass through the objective lens, a center of the ring reflector, and the focusing module in sequence, and then reach the image sensing acquisition module.

Further, the objective lens includes at least one lens group, and optical lenses in the at least one lens group are all coated with anti-reflection coating.

Further, the main optical assembly further includes an optical path folding reflector, the objective lens is located at one side of the optical path folding reflector, and the focusing module and the image sensing acquisition module are located at the other side of the optical path folding reflector.

An axial compensator is provided between the ring reflector and the optical path folding reflector, and a lateral compensator is provided between the focusing module and the image sensing acquisition module.

Further, the illumination module includes a plurality of light-emitting diodes, and light emitted by the plurality of light-emitting diodes has mutually different wavelengths. Each of the plurality of light-emitting diodes corresponds to a narrow-band spectrum with a bandwidth of less than 30 nm, and a spectral range of the plurality of light-emitting diodes is from 480 nm to 980 nm.

Further, the plurality of light-emitting diodes are configured to flash illumination light of a specific wavelength one by one in a predetermined light-emitting sequence and light-emitting time; or, the plurality of light-emitting diodes are configured to emit light at the same time.

Further, the illumination module further includes a light emission monitor configured to monitor luminous energy of each light-emitting diode and turn off the light source when the luminous energy reaches a preset energy limit.

Further, the light emission monitor includes a photoelectric sensor and an electronic switch.

Further, the illumination light emitted by the illumination module is conducted to form a plurality of arc-shaped illumination areas evenly distributed along a same circumference, and a gap is defined between the adjacent arc-shaped illumination areas.

Further, a number of the arc-shaped illumination areas is two, and center angles corresponding to the two arc-shaped illumination areas are both less than 180 degrees.

The illumination module is configured to emit illumination light forming any one of the two arc-shaped illumination areas, or illumination light forming the two arc-shaped illumination areas simultaneously.

Further, the illumination module includes a first illumination unit and a second illumination unit independent of the first illumination unit, illumination light emitted by the first illumination unit is conducted to form one of the two arc-shaped illumination areas, and illumination light emitted by the second illumination unit is conducted to form the other one of the two arc-shaped illumination areas.

Further, a number of the arc-shaped illumination areas is four, and center angles corresponding to the four arc-shaped illumination areas are all less than 90 degrees.

The illumination module is configured to emit illumination light forming any one of the four arc-shaped illumination areas, or illumination light forming the four arc-shaped illumination areas simultaneously, or illumination light forming any two of the four arc-shaped illumination areas simultaneously.

Further, the illumination module includes a first illumination unit and a second illumination unit, illumination light emitted by the first illumination unit is configured to form two arc-shaped illumination areas located at diagonal positions, and illumination light emitted by the second illumination unit is configured to form the other two arc-shaped illumination areas located at diagonal positions.

Further, the first illumination unit and the second illumination unit are configured to emit light alternately or simultaneously.

Further, illumination light emitted by the illumination module is conducted to form a plurality of ring-shaped illumination areas distributed outward from a same axis, with a larger ring outside and a smaller ring inside.

Further, a number of the ring-shaped illumination areas is two, and the two ring-shaped illumination areas are configured to form two illumination rings, and an inner diameter of an inner ring of the illumination ring and an outer diameter of an outer ring of the illumination ring are both within a specific illumination ring size specification.

Further, the illumination module includes a first illumination unit and a second illumination unit independent of the first illumination unit. Illumination light emitted by the first illumination unit is configured to form an outer illumination ring, and illumination light emitted by the second illumination unit is configured to form an inner illumination ring.

Further, the fundus camera further includes a sight target module configured to guide the eye of the patient to look in different directions.

Further, the sight target module includes a plurality of light-emitting points distributed in multiple rows, and the plurality of light-emitting points in each row are evenly distributed, the plurality of light-emitting points at different coordinates are configured to emit light individually and guide the eye of the patient to look in directions of the plurality of light-emitting points to realize imaging of different parts of the retina.

Further, the sight target module includes a micro-mirror matrix image generator.

Further, the fundus camera further includes an alignment module provided outside the main optical assembly.

The alignment module includes a near infrared light-emitting diode and a non-coaxial camera.

Further, the fundus camera further includes a central control module in signal connection with the illumination module, the focusing module, the image sensing acquisition module, the sight target module and the alignment module. The central control module is configured to operate on a designated computing platform including a central processor, a co-processor, and a graphics processing unit. Further, the fundus camera further includes a display connected to the central control module. The alignment module and the display are arranged on opposite sides of the main optical assembly.

Further, the central control module includes a real-time high-function embedded control software module operated on a computing platform with high-capacity, high-performance and high-speed.

Further, the fundus camera further includes a filter disc located between the image sensing acquisition module and the focusing module, and the filter disc is provided with a plurality of optical filter evenly distributed around an axial direction of the filter disc.

The fundus camera provided by the present application includes: an illumination module, a main optical assembly, a focusing module, and an image sensing acquisition module. The illumination module includes a plurality of light sources configured to emit light of different wavelengths, illumination light emitted by the plurality of light sources is conducted to enter an eye of a patient through the main optical assembly, and light reflected by a retina of the patient is conducted to pass through the main optical assembly and the focusing module to enter the image sensing acquisition module. When using the fundus camera provided by the present application to examine the patient's eyes, multiple light sources emit light of different wavelengths. Since the reflection and absorption of the retina depends on the spectrum, different wavelengths penetrate the retina at different depths, so that different layers of the retina at different depths can be imaged to provide valuable medical and diagnostic data.

BRIEF DESCRIPTION OF THE DRAWINGS

In order to more clearly explain the specific embodiments of the present application or the technical solutions in the prior art, the following will briefly introduce the drawings required for the specific embodiments or the description of the prior art. Obviously, the drawings in the following description are some embodiments of the present application. For those of ordinary skill in the art, without paying any creative labor, other drawings can also be obtained based on these drawings.

Reference numerals: 100—illumination module; 110—field lens; 120—illumination optical path aperture; 130—filter disc;

131—filter; 200—main optical assembly; 210—ring reflector; 220—objective lens; 230—optical path folding reflector; 240—axial compensator; 250—lateral compensator; 300—focusing module; 400—image sensing acquisition module; 500—sight target module; 510—beam splitter; 600—alignment module; 700—display; 800—central control module.

DETAILED DESCRIPTION OF THE EMBODIMENTS

The technical solutions of the present application will be described clearly and completely below with reference to the drawings. Obviously, the described embodiments are part of the embodiments of the present application, but not all of the embodiments. Based on the embodiments in the present application, all other embodiments obtained by those of ordinary skill in the art without making creative efforts fall within the protection scope of the present application.

In the description of this application, it should be noted that the terms "center", "upper", "lower", "left", "right", "vertical", "horizontal", "inner", "outer", etc. indicate the orientation or positional relationship based on the orientation or positional relationship shown in the drawings, only for the convenience of describing the present application and simplify the description, rather than indicating or implying that the device or element referred to must have a specific orientation, be constructed and operate in a specific orientation, and therefore cannot be construed as limiting the present application. In addition, the terms "first", "second", and "third" are for descriptive purposes only, and cannot be understood as indicating or implying relative importance.

In the description of the present application, it should be noted that the terms "installation", "link", and "connection" should be understood in a broad sense, for example, it may be a fixed connection or a removable connection, or an integral connection; it may be either mechanical connection or electrical connection; it may be direct connection, or indirect connection through an intermediary, or internal connection between two components. For those of ordinary skill in the art, the specific meaning of the above terms in the present application may be understood in specific situations.

Figure 1:
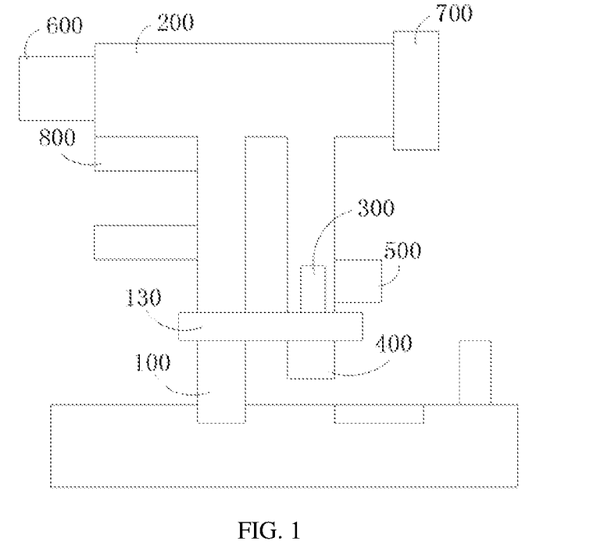
FIG. 1 is a schematic structural diagram of a fundus camera provided by an embodiment of the present application.

FIG. 1 is a schematic structural diagram of a fundus camera provided by an embodiment of the present application. As shown in FIG. 1, the fundus camera provided by the present application includes: an illumination module 100, a main optical assembly 200, a focusing module 300, and an image sensing acquisition module 400. The illumination module 100 includes a plurality of light sources configured to emit light of different wavelengths, illumination light emitted by the plurality of light sources is conducted to enter an eye of a patient through the main optical assembly 200, and light reflected by a retina of the patient is conducted to pass through the main optical assembly 200 and the focusing module 300 to enter the image sensing acquisition module 400.

Specifically, the illumination module 100, the focusing module 300, and the image sensing acquisition module 400 are all located below the main optical assembly 200. The focusing module 300 adjusts the focal length to compensate for the diopter of the patient's eye, so that a clear image may be collected. The image sensing acquisition module 400 includes an image sensor, and the image sensor is configured to acquire an image.

Figure 2:
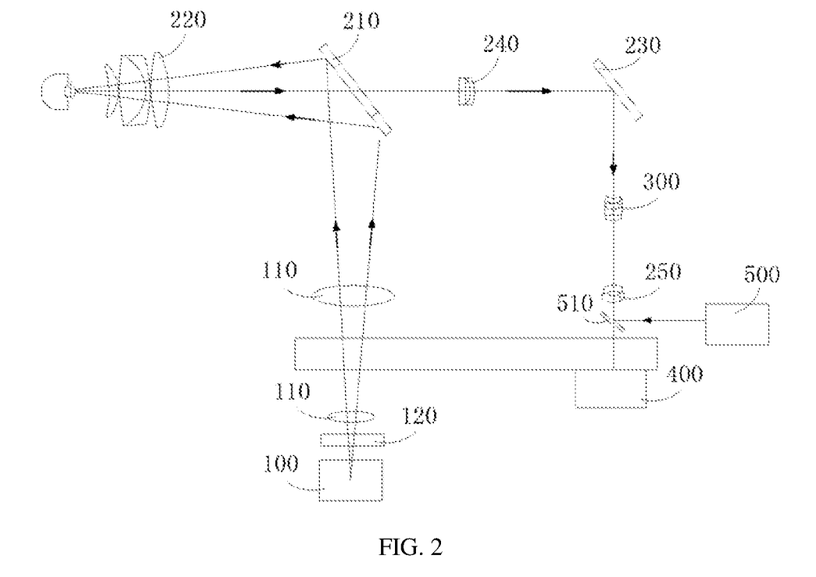
FIG. 2 is a schematic diagram of an optical path of the fundus camera provided by an embodiment of the present application.

In one embodiment, referring to a schematic diagram of an optical path of the fundus camera shown in FIG. 2, it simply illustrates that the main optical assembly 200 includes a ring reflector 210 and an objective lens 220, and the ring reflector 210 is arranged obliquely. Illumination light emitted from the illumination module 100 is reflected to the objective lens 220 by the ring reflector 210, and then is configured to enter the patient's eye. Light reflected by the patient's retina is conducted to pass through the objective lens 220, a center of the ring reflector 210, and the focusing module 300 in sequence, and then reach the image sensing acquisition module 400. The image sensing acquisition module 400 may include an image sensor.

As shown in FIG. 2, the objective lens 220 is located on a left side of the ring reflector 210, the illumination module 100 is located on a lower side of the ring reflector 210 and an input end of the illumination optical path. The ring reflector 210 is arranged obliquely and a reflective surface of the ring reflector 210 is opposite to the objective lens 220 and the illumination module 100, respectively. An included angle between a central axis of the ring reflector and a plane where the objective lens is located is within a specified angle range, such as between 20 degrees to 60 degrees, 45 degrees to 60 degrees, etc. The specified angle range may be flexibly set according to needs, which is not limited here. In an embodiment, the included angle between the central axis of the ring reflector and the plane where the objective lens is located may be 45 degrees.

The illumination light emitted by the illumination module 100 is transmitted to the input end of the illumination optical path through the optical fiber. Through the illumination imaging lens system and the ring reflector 210, the illumination light is reflected to the objective lens 220 by the ring reflector 210, and the illumination light is refracted by the objective lens 220. The objective lens 220 is a common optical path for illumination and observation, it forms a field of view at a large angle and the projection focus is projected into the focal plane at the designed working distance (the distance between the pupil of the eye and the front surface of the lens). The reflected retinal signal passes through the objective lens 220, the central hole of the ring reflector 210 and the focusing module 300 in sequence, then reaches the image sensing acquisition module 400, and the image sensing acquisition module 400 collects images.

Further, the objective lens 220 includes one or more lens groups, and optical lenses in the lens groups are all coated with a multiple layers of anti-reflection coating. Different anti-reflection coating corresponds to different wavelengths to improve the anti-reflection performance as much as possible, thereby reducing unnecessary reflections.

Further, the fundus camera is further provided with an optical lens for imaging and an optical lens with other functions. The optical lenses are all coated with an anti-reflection coating to reduce unnecessary reflection.

Further, the main optical assembly 200 further includes an optical path folding reflector 230, the objective lens 220 is located at one side of the optical path folding reflector 230, and the focusing module 300 and the image sensing acquisition module 400 are located at the other side of the optical path folding reflector 230. An axial compensator 240 is provided between the ring reflector 210 and the optical path folding reflector 230, and a lateral compensator 250 is provided between the focusing module 300 and the image sensing acquisition module 400.

Specifically, the optical path folding reflector 230 is disposed on a side of the ring reflector 210 facing away from the objective lens 220. The optical path folding reflector 230 is arranged obliquely. The focusing module 300 and the image sensing acquisition module 400 are both located on a lower side of the optical path folding reflector 230. The focusing module 300 is located between the optical path folding reflector 230 and the image sensing acquisition module 400. The axial compensator 240 is located between the ring reflector 210 and the optical path folding reflector 230, and the lateral compensator 250 is located between the focusing module 300 and the image sensing acquisition module 400.

After the light reflected by the patient's retina passes through the center of the ring reflector 210, it passes through the axial compensator 240 and the optical path folding reflector 230. The axial compensator 240 is configured to adjust an axial tolerance and alignment of the optical axis. The imaged light is reflected to the focusing module 300 by the optical path folding reflector 230, and the reflected light passes through the focusing module 300 and the lateral compensator 250 in sequence. The lateral compensator 250 is configured to adjust a tolerance and alignment on a plane perpendicular to the optical axis, and the adjusted light enters the image sensing acquisition module 400.

Further, the illumination module 100 includes one or more illumination units. Each illumination unit has a plurality of light-emitting diodes, and the light emitted by the plurality of light-emitting diodes has mutually different wavelengths.

Multispectral vision imaging divides the entire spectrum from blue to near infrared (480 nm to 980 nm) into different relatively narrow spectral bands, and each light-emitting diode has a specific spectrum with a relatively limited wavelength and width, which together cover a wider range of spectrum. That is, each light-emitting diode corresponds to a different spectral band, and a plurality of the light-emitting diodes have a spectral coverage ranging from 480 nm to 980 nm. Each light-emitting diode corresponds to a narrow-band spectrum such as a bandwidth below 30 nm. In specific implementation, the distribution of multi-spectral light sources ensures that light sources of various wavelengths can evenly illuminate the fundus. In addition, the fundus camera of the present application may maintain a certain distance between a cross section of an entrance optical path and a cross section of an exit optical path at the pupil of the eye, so as to overcome the interference on the image caused by unwanted backscattering of the fundus. Specifically, the light emitted by the light-emitting diode is transmitted to an input end of the illumination optical path of the main optical assembly 200 through an optical coupling unit of the illumination module 100, and passes through the illumination optical path aperture 120, the illumination optical path eye lens and the field lens 110 to image on the pupil of the patient, and then illuminate the entire retina within a predetermined solid angle (field of view).

Further, the illumination unit may combine light-emitting diodes in different forms.

Further, the optical coupling unit may be composed of an optical lens, a prism, or a cone lens system, or may be composed of a single or multiple optical fibers, or may be composed of a single or multiple optical fibers combined with a uniform light device, or may be composed of blank space.

Further, the optical coupling unit is composed of multiple optical fibers combined with a uniform light device (for example, a uniform light rod). The reflection of light on the inner side of the uniform light rod is basically an ideal total reflection. The recommended length of the uniform light bar may be between 10 nm and 30 mm. Further, the illumination module 100 has two illumination units, which are coordinated by the illumination module 100 respectively, and emit light individually or simultaneously according to the instructions of the central control module 800 of the fundus camera.

Further, a plurality of light-emitting diodes of the illumination unit are configured to flash illumination light of a specific wavelength one by one in a predetermined or specified sequence and light-emitting time, but it is also possible to make the plurality of light-emitting diodes emit light at the same time according to the application requirements, and the light-emitting time may be set in advance. The image sensing acquisition module 400 exposes a series of images corresponding to each light source and synchronously collected with the light-emitting diodes flash, and the collected original retinal images are transmitted to an external computing device through the central control module 800 to be configured for storage, reading or further processing. In normal applications, the retinal images illuminated by the spectrum of each light-emitting diode are collected separately.

Further, the illumination module 100 may also adopt a synchronous flash phase acquisition mode, that is, when the illumination module 100 receives a lighting instruction or a lighting trigger pulse from the central control module 800, the corresponding light-emitting diode emits light according to the specified flash time. The control module in the fundus camera may simultaneously send signals to the illumination module 100 and the image sensing acquisition module 400, or the illumination module 100 may simultaneously send signals to the image sensing acquisition module 400 immediately after starting to emit light, so that the image sensing acquisition module 400 may work synchronously with the illumination module 100.

Further, the illumination module 100 further has functions of light energy monitoring and energy value cutoff. In specific implementation, the illumination module further includes a light emission monitor configured to monitor luminous energy of each light-emitting diode and turn off the light source when the luminous energy reaches a preset energy limit. The output optical power and energy of each light-emitting diode are calibrated and real-time monitored by the light-emitting monitor to realize real-time monitoring of the energy of each light-emitting diode each time it emits light and during normal or abnormal operation, once the energy reaches the safe energy warning limit, cut off the light source immediately to ensure absolute safety protection for the patient. In one embodiment, the above-mentioned light-emitting monitor may include a photosensor and an electronic switch.

Specifically, the illumination module 100 is provided with a photoelectric sensor. The photoelectric sensor is configured to monitor the output optical power and energy of each light-emitting diode in real time. The photoelectric sensor compares the collected energy value with the set energy value through the comparator. When the collected energy value reaches the set energy value, the electronic switch controls the light source and immediately cuts off the light source to prevent damage to the patient's eyes.

Further, the illumination light emitted by the illumination module 100 is conducted to form a plurality of arc-shaped illumination areas evenly distributed along a same circumference, and a gap is defined between the adjacent arc-shaped illumination areas.

In some embodiments, a number of the arc-shaped illumination areas is two, and center angles corresponding to the two arc-shaped illumination areas are both less than 180 degrees. The illumination module 100 is configured to emit illumination light forming any one of the two arc-shaped illumination areas, or illumination light forming the two arc-shaped illumination areas simultaneously.

The two arc-shaped illumination areas are approximately semicircular, and the corresponding center angles are equal, and the two arc-shaped illumination areas are relatively arranged on the same circumference.

Each arc-shaped illumination area originates from a corresponding illumination unit inside the illumination module 100. The two illumination units are configured to illuminate the same field-of-view area of the patient's retina. The illumination module 100 brings the light beam provided by the corresponding illumination unit to the input end of the illumination optical path, so that the image is nearly semicircular on the pupil of the eye under test, thereby further illuminating the entire retina within a predetermined solid angle (field of view) through the illumination optical path.

Further, the illumination module 100 has two independently controllable illumination units inside, namely, a first illumination unit and a second illumination unit, and the two illumination units have their own light-emitting diode combinations. Each illumination unit provides illumination light to its respective ring.

Further, illumination light emitted by the illumination module is conducted to form a plurality of ring-shaped illumination areas distributed outward from a same axis, with a larger ring outside and a smaller ring inside.

In one embodiment, a number of the ring-shaped illumination areas is two, and the two ring-shaped illumination areas are configured to form two illumination rings, and an inner diameter of an inner ring of the illumination ring and an outer diameter of an outer ring of the illumination ring are both within a specific illumination ring size specification.

In addition, the first illumination unit and the second illumination unit may be independent of each other. Illumination light emitted by the first illumination unit is configured to form an outer illumination ring, and illumination light emitted by the second illumination unit is configured to form an inner illumination ring.

During the use of the fundus camera, the two illumination units alternately emit light. Specifically, after one illumination unit of the illumination module 100 (responsible for forming the first arc-shaped illumination area) emits illumination light of wavelength 1, the other illumination unit (responsible for forming the second arc-shaped illumination area) then emits illumination light of wavelength 1, then, after the first illumination unit emits illumination light of wavelength 2, the second illumination unit also emits illumination light of wavelength 2, successively, and so on. While each illumination unit is illuminating, the image sensing acquisition module 400 simultaneously performs image acquisition. In addition, the two illumination units may simultaneously emit light to form a ring-shaped illumination area.

In a specific working distance and wide-angle fundus camera, each image has a reflection contribution from the corneal surface. Due to the use of alternating semi-ring area illumination, two separate captured images at the same wavelength may be processed using special image processing algorithms and re-combined to obtain an image without corneal specular reflection. In addition, segmented illumination is used, this digital image processing and image repair algorithms will improve the final overall image results.

In other embodiments, a number of the arc-shaped illumination areas is four, and center angles corresponding to the four arc-shaped illumination areas are all less than 90 degrees. The illumination module 100 is configured to emit illumination light forming any one of the four arc-shaped illumination areas, or illumination light forming the four arc-shaped illumination areas simultaneously, or illumination light forming any two of the four arc-shaped illumination areas simultaneously.

Specifically, in the four-arc illumination mode, the illumination light is provided by two independent illumination units of the illumination module 100, namely, the first illumination unit and the second illumination unit. Each corresponding illumination unit of the illumination module 100 will divide the output illumination light into two parts, thereby forming two opposite but not adjacent arc-shaped illumination areas.

Further, the illumination module 100 brings the four arc-shaped light beams provided by the two corresponding illumination units to the input end of the illumination optical path, each arc-shaped being a nearly quarter-ring. The illumination optical path through the main optical assembly 200 is imaged on the pupil of the eye to be tested, thereby further illuminating the entire retina within a predetermined solid angle (field of view) through the illumination optical path.

Specifically, each illumination unit of the illumination module 100 will illuminate two opposing quarter rings.

During the use of the fundus camera, the two illumination units alternately emit light. Specifically, after one illumination unit of the illumination module 100 (responsible for forming the first and the third arc-shaped illumination areas) emits illumination light of wavelength 1, the other illumination unit (responsible for forming the second and the fourth arc-shaped illumination areas) then emits illumination light of wavelength 1, then, after the first illumination unit emits illumination light of wavelength 2, the second illumination unit also emits illumination light of wavelength 2, successively, and so on. While each side of illumination units are illuminating, the image sensing acquisition module 400 simultaneously performs image acquisition. Specifically, the first arc-shaped illumination area, the second arc-shaped illumination area, the third arc-shaped illumination area, and the fourth arc-shaped illumination area are sequentially arranged along the circumferential direction.

Certainly, the above only illustrates embodiments in which the number of arc-shaped illumination areas is two and four. In practical applications, the number of arc-shaped illumination areas may also be flexibly set according to needs, which is not limited herein.

In summary, with the above-mentioned illumination module provided in this embodiment, the fundus camera provided in this embodiment may better implement fundus imaging of multi-spectral light sources, and may achieve the following functions:

(1) dividing a single source into multiple narrow-band spectra (such as a bandwidth below 30 nm), or integrating multiple narrow-band spectra into a single light source, so as to obtain retinal imaging;

(2) effectively controlling the illumination power so that the daily exposure is far below the safety threshold level;

(3) capturing multiple images (multiple wavelength images) within one frame, the frame length may be less than 250 ms;

(4) combining a single wavelength or a sequence of different wavelengths that are repeated multiple times in a single frame;

(5) supply circular multi-spectral light to realize fundus illumination with wide angle of view;

(6) enabling the system to flexibly configure different light sources due to the modular design of the light source; and (7) adjusting the luminous power according to the measured feedback results of the retinal reflective characteristics.

Figure 3:
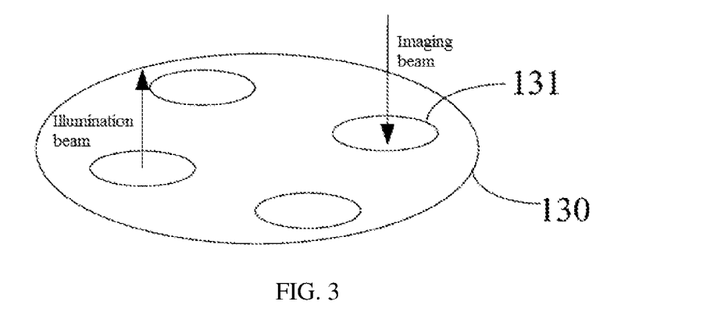
FIG. 3 is a schematic structural diagram of a filter disc provided by an embodiment of the present application.

Further, the fundus camera further includes a filter disc 130, which is located between the two field lenses 110, and is also located between the image sensing acquisition module 400 and the focusing module 300. A beam splitter 510 is further provided between the image sensing acquisition module 400 and the focusing module 300. In a specific implementation, the filter disc 130 may be disposed between the image sensing acquisition module 400 and the beam splitter 510. The filter disc 130 is provided with multiple filters, and the multiple filters are evenly distributed around the axial direction of the filter disc 130. The filter disc 130 provides separate filters for the illumination beam and the observation beam, and the filters play the role of filtering and changing the light. As shown in FIG. 3, a structural schematic diagram of a filter disc is provided, a plurality of filters 131 (only four are schematically shown in FIG. 3) are provided on the filter disc 130, which are respectively configured to perform light processing on the illumination beam and the imaging beam (that is, the aforementioned observation beam). The filter disc shown in FIG. 3 may also be referred to as a two-pass filter disc.

The filter disc 130 is controlled and rotated by the control motor. For the illumination optical path and the imaging optical path, when the filter disc 130 is driven and rotated by the control motor, the filter configured for the illumination optical path to pass through and the filter configured for the imaging optical path to pass through are always switched with the exact lock step.

Further, the fundus camera further includes a sight target module 500 configured to guide the eye of the patient to look in different directions, so that different parts of the retina may be imaged.

Specifically, the sight target module 500 is located to the right of the beam splitter 510 in the imaging optical path of the main optical assembly 200. The sight target module 500 and the image sensor are on the same imaging plane, but the sight target module 500 is separately installed and arranged through the beam splitter 510. The light emitted by the sight target module 500 is reflected by the beam splitter 510 to the main optical assembly 200.

Figure 4:
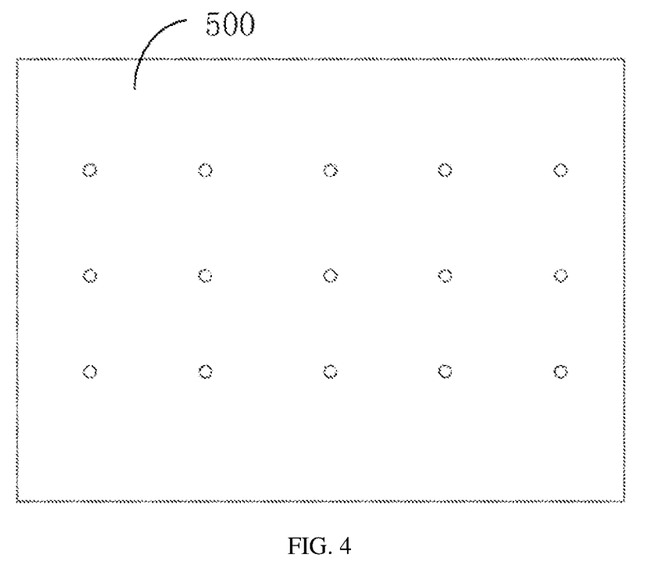
FIG. 4 is a schematic diagram of a sight target module of the fundus camera provided by an embodiment of the present application.

In one embodiment, as shown in FIG. 4, the sight target module 500 has multiple light-emitting points (not limited to 15 in FIG. 3), and the multiple light-emitting points are distributed in multiple rows, such as forming a N*M light-emitting diodes array; where, the values of N and M may be the same or different. The multiple light-emitting points in each row are evenly distributed, and the light-emitting points at different coordinates emit light individually according to the image acquisition requirements, guiding the eyes to look in the direction of the (different) light-emitting points, so that different parts of the retina are imaged. The function of displaying position of the sight target module 500 may be implemented by different methods, such as a light-emitting diode array, being based on a liquid crystal display, or a dynamic micro-mirror matrix. Both the liquid crystal display and the micro-mirror matrix have high-resolution and fully programmable image generators.

In one embodiment, the sight target module 500 is composed of a fully programmable micro-mirror matrix (DMD) image generator with high resolution based on a liquid crystal display or a dynamic digital micro-mirror matrix device. Further, the fundus camera further includes an alignment module 600 provided outside the main optical assembly 200. The alignment module 600 includes a near infrared light-emitting diode and a non-coaxial camera.

Specifically, the fundus camera further includes a display 700, and the alignment module 600 and the display 700 are disposed on opposite sides of the main optical assembly 200.

Further, the alignment module 600 uses two near-infrared light-emitting diodes. The two near-infrared light-emitting diodes are located above both sides of the objective lens 220 of the main optical assembly 200, and the non-coaxial camera is located on the lower side of the objective lens 220 of the main optical assembly 200.

During the test, the patient faces the fundus camera, the operator faces the display 700 and operates on the other side of the fundus camera. The patient places his head on the jaw holder in front of the fundus camera, and looks one eye under test toward the center of the objective lens 220. The near-infrared light-emitting diodes in the alignment module 600 illuminate the front of the eye, and the non-coaxial camera collects the image of the front of the eye, and the image is directly and continuously transmitted to the display 700 through the central control module 800 to guide the operator to align the optical axis of the instrument with the center of the patient's pupil. Then, focal length adjustments are made to compensate for the diopter of the individual's eye, so that a clear image may be collected. After adjusting the focus, the light-emitting diodes will flash in a preset order. The image sensor exposure will be synchronized with the flash, and a series of retinal images are collected, which are one-to-one corresponding to images of each light-emitting diode, and then these original retinal images are transferred to an external computing device to be configured for storage, reading, or further processing.

Further, the fundus camera further includes a central control module 800 in signal connection with the illumination module 100, the focusing module 300, the image sensing acquisition module 400, the sight target module 500 and the alignment module 600.

The central control module 800 coordinates and controls the operation of the entire fundus camera, including the coordination and control of the illumination module 100, the focusing module 300, the image sensing acquisition module 400, the alignment module 600, and the sight target module 500. The central control module 800 manages simultaneously all images transmitted to the display and interface module, and accept and coordinate the execution of all instructions input by the operator through the display and interface module.

Further, the central control module 800 includes a real-time high-function embedded control software module operated on a computing platform with high-capacity, high-performance and high-speed.

The monitoring, control and coordination of the fundus camera are managed by the central control module 800.

Further, the computing platform of the central control module 800 is composed of a powerful central processing unit (CPU), a co-processor, and a graphics processing unit (GPU).

Further, the computing platform of the central control module 800 further includes a dedicated port for coordination of various functional modules.

Further, the computing platform of the central control module 800 further includes accurate timing pulses controlled by a real-time high-function embedded control software module and created by programmable logic such as FPGA to provide accurate trigger signals, receive action confirmation, and other management controls such as sequence and reset. In the specific implementation, the embedded control software module may include a hardware abstraction layer, a microservice-based application program, a display, and a graphical user interface, etc., and has a high degree of modularity and scalability.

The fundus camera provided by one embodiment of the present application includes: an illumination module 100, a main optical assembly 200, a focusing module 300, and an image sensing acquisition module 400. The illumination module 100 includes a plurality of light sources configured to emit light of different wavelengths, illumination light emitted by the plurality of light sources is conducted to enter an eye of a patient through the main optical assembly 200, and light reflected by a retina of the patient is conducted to pass through the main optical assembly 200 and the focusing module 300 to enter the image sensing acquisition module 400. When using the fundus camera provided by one embodiment of the present application to examine the patient's eyes, multiple light sources emit light of different wavelengths. Since the reflection and absorption of the retina depends on the spectrum, different wavelengths penetrate the retina at different depths, so that different layers of the retina at different depths can be imaged to provide valuable medical and diagnostic data.

Finally, it should be noted that the above embodiments are only used to illustrate the technical solutions of the present application, but not to limit them. Although the present application has been described in detail with reference to the foregoing embodiments, those of ordinary skill in the art should understand that: the technical solutions described in the foregoing embodiments may still be modified, or some or all of the technical features thereof may be equivalently replaced; and these modifications or replacements do not deviate the essence of the corresponding technical solutions from the scope of the embodiments of the present application.

INDUSTRIAL APPLICABILITY

By applying the technical solution of the present application, multiple light sources emit light of different wavelengths. Since the reflection and absorption of the retina depends on the spectrum, different wavelengths penetrate the retina at different depths, so that different layers of the retina at different depths can be imaged to provide valuable medical and diagnostic data.

What is claimed is:

1. A fundus camera, comprising: an illumination module, a main optical assembly, a focusing module, and an image sensing acquisition module; the illumination module comprises a plurality of light sources configured to emit light of different wavelengths, illumination light emitted by the plurality of light sources is conducted to enter an eye of a patient through the main optical assembly, and light reflected by a retina of the patient is conducted to pass through the main optical assembly and the focusing module to enter the image sensing acquisition module;

wherein the illumination light emitted by the illumination module is conducted to form a plurality of arc-shaped illumination areas evenly distributed along a same circumference, and a gap is defined between the adjacent arc-shaped illumination areas.

2. The fundus camera according to claim 1, wherein the main optical assembly comprises a ring reflector and an objective lens, the ring reflector is arranged obliquely, a reflecting surface of the ring reflector is respectively opposite to the objective lens and the illumination module, and an included angle between a central axis of the ring reflector and a plane where the objective lens is located is within a specified angle range; the illumination light emitted by the illumination module is reflected to the objective lens by the ring reflector, and then is configured to enter the eye of the patient; the light reflected by the retina of the patient is conducted to pass through the objective lens, a center of the ring reflector, and the focusing module in sequence, and then reach the image sensing acquisition module.

3. The fundus camera according to claim 2, wherein the objective lens comprises at least one lens group, and optical lenses in the at least one lens group are all coated with multiple layers of anti-reflection coating, wherein different anti-reflection coating corresponds to different wavelengths.

4. The fundus camera according to claim 2, wherein the main optical assembly further comprises an optical path folding reflector, the objective lens is located at one side of the optical path folding reflector, and the focusing module and the image sensing acquisition module are located at the other side of the optical path folding reflector; an axial compensator is provided between the ring reflector and the optical path folding reflector, and a lateral compensator is provided between the focusing module and the image sensing acquisition module.

5. The fundus camera according to claim 1, wherein the illumination module comprises a plurality of light-emitting diodes, each of the plurality of light-emitting diodes corresponds to a narrow-band spectrum with a bandwidth of less than 30 nm, and a spectral range of the plurality of light-emitting diodes is from 480 nm to 980 nm.

6. The fundus camera according to claim 5, wherein the plurality of light-emitting diodes are configured to flash illumination light of a specific wavelength one by one in a predetermined light-emitting sequence and light-emitting time; or, the plurality of light-emitting diodes are configured to emit light at the same time.

7. The fundus camera according to claim 5, wherein the illumination module further comprises a light emission monitor configured to monitor luminous energy of each light-emitting diode and turn off the light source when the luminous energy reaches a preset energy limit.

8. The fundus camera according to claim 7, wherein the light emission monitor comprises a photoelectric sensor and an electronic switch.

9. The fundus camera according to claim 1, wherein a number of the arc-shaped illumination areas is two, and center angles corresponding to the two arc-shaped illumination areas are both less than 180 degrees; the illumination module is configured to emit illumination light forming any one of the two arc-shaped illumination areas, or illumination light forming the two arc-shaped illumination areas simultaneously.

10. The fundus camera according to claim 9, wherein the illumination module comprises a first illumination unit and a second illumination unit independent of the first illumination unit, illumination light emitted by the first illumination unit is conducted to form one of the two arc-shaped illumination areas, and illumination light emitted by the second illumination unit is conducted to form the other one of the two arc-shaped illumination areas.

11. The fundus camera according to claim 9, wherein the first illumination unit and the second illumination unit are configured to emit light alternately or simultaneously.

12. The fundus camera according to claim 1, wherein a number of the arc-shaped illumination areas is four, and center angles corresponding to the four arc-shaped illumination areas are all less than 90 degrees; the illumination module is configured to emit illumination light forming any one of the four arc-shaped illumination areas, or illumination light forming the four arc-shaped illumination areas simultaneously, or illumination light forming any two of the four arc-shaped illumination areas simultaneously.

13. The fundus camera according to claim 12, wherein the illumination module comprises a first illumination unit and a second illumination unit, illumination light emitted by the first illumination unit is configured to form two arc-shaped illumination areas located at diagonal positions, and illumination light emitted by the second illumination unit is configured to form the other two arc-shaped illumination areas located at diagonal positions.

14. The fundus camera according to claim 1, further comprising a sight target module configured to guide the eye of the patient to look in different directions.

15. The fundus camera according to claim 14, wherein the sight target module comprises a plurality of light-emitting points distributed in multiple rows, and the plurality of light-emitting points in each row are evenly distributed, the plurality of light-emitting points at different coordinates are configured to emit light individually and guide the eye of the patient to look in directions of the plurality of light-emitting points to realize imaging of different parts of the retina.

16. The fundus camera according to claim 15, wherein the sight target module comprises a micro-mirror matrix image generator.

17. The fundus camera according to claim 14, further comprising an alignment module provided outside the main optical assembly and comprising a near infrared light-emitting diode and a non-coaxial camera.

18. The fundus camera according to claim 17, further comprising a central control module in signal connection with the illumination module, the focusing module, and the image sensing acquisition module, the sight target module and the alignment module; the central control module is configured to operate on a designated computing platform comprising a central processor, a co-processor, and a graphics processing unit; the fundus camera further comprises a display connected to the central control module; the alignment module and the display are arranged on opposite sides of the main optical assembly.

19. The fundus camera according to claim 1, further comprising a filter disc located between the image sensing acquisition module and the focusing module, and the filter disc is provided with a plurality of optical filter evenly distributed around an axial direction of the filter disc.

* * * * *